US012596108B2

(12) United States Patent
Marty et al.

(10) Patent No.: US 12,596,108 B2
(45) Date of Patent: Apr. 7, 2026

(54) AUTOMATED LIPID EXCHANGE-MASS SPECTROMETRY SYSTEMS AND METHODS

(71) Applicant: ARIZONA BOARD OF REGENTS ON BEHALF OF THE UNIVERSITY OF ARIZONA, Tucson, AZ (US)

(72) Inventors: Michael Marty, Tucson, AZ (US); James Keener, Tucson, AZ (US); Guozhi Zhang, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 913 days.

(21) Appl. No.: 17/796,054

(22) PCT Filed: Feb. 4, 2021

(86) PCT No.: PCT/US2021/016558
§ 371 (c)(1),
(2) Date: Jul. 28, 2022

(87) PCT Pub. No.: WO2021/158750
PCT Pub. Date: Aug. 12, 2021

(65) Prior Publication Data
US 2023/0057500 A1     Feb. 23, 2023

Related U.S. Application Data

(60) Provisional application No. 62/970,884, filed on Feb. 6, 2020.

(51) Int. Cl.
*B01L 3/00* (2006.01)
*B01D 15/08* (2006.01)
(Continued)

(52) U.S. Cl.
CPC ......... *G01N 30/7233* (2013.01); *G01N 30/30* (2013.01); *G01N 33/58* (2013.01);
(Continued)

(58) Field of Classification Search
CPC .... G01N 30/7233; G01N 30/30; G01N 33/58; G01N 33/92; G01N 35/0099;
(Continued)

(56) References Cited

U.S. PATENT DOCUMENTS

| | | | | |
|---|---|---|---|---|
| 2005/0152984 A1* | 7/2005 | Sligar | .................... | C07K 14/47 |
| | | | | 435/7.1 |
| 2011/0104781 A1* | 5/2011 | Katzen | .................... | C07K 1/02 |
| | | | | 435/254.22 |

OTHER PUBLICATIONS

Anderson, Kyle W., Elyssia S. Gallagher, and Jeffrey W. Hudgens. "Automated removal of phospholipids from membrane proteins for H/D exchange mass spectrometry workflows." Analytical chemistry 90.11 (2018): 6409-6412. (Year: 2018).*

(Continued)

*Primary Examiner* — Jennifer Wecker
*Assistant Examiner* — Oyeleye Alexander Alabi
(74) *Attorney, Agent, or Firm* — NGUYEN TARBET IP LAW

(57) ABSTRACT

An automated system for lipid exchange-mass spectrometry, e.g., measuring affinity of a membrane protein for lipids. The automated systems herein can measure the specificity of membrane protein-lipid interactions, detect remodeling of the membrane environment, and determine optimal lipid composition for membrane proteins.

20 Claims, 2 Drawing Sheets

(51) Int. Cl.

| | |
|---|---|
| *B01F 33/302* | (2022.01) |
| *B01F 33/3033* | (2022.01) |
| *B01L 7/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C12M 1/34* | (2006.01) |
| *C12M 3/06* | (2006.01) |
| *C12N 1/14* | (2006.01) |
| *C12N 1/20* | (2006.01) |
| *C12Q 1/02* | (2006.01) |
| *C12Q 1/6806* | (2018.01) |
| *C12Q 1/6844* | (2018.01) |
| *C12Q 1/6848* | (2018.01) |
| *C12Q 1/686* | (2018.01) |
| *G01N 15/10* | (2024.01) |
| *G01N 15/14* | (2024.01) |
| *G01N 15/1433* | (2024.01) |
| *G01N 21/29* | (2006.01) |
| *G01N 21/65* | (2006.01) |
| *G01N 30/02* | (2006.01) |
| *G01N 30/30* | (2006.01) |
| *G01N 30/72* | (2006.01) |
| *G01N 33/543* | (2006.01) |
| *G01N 33/557* | (2006.01) |
| *G01N 33/574* | (2006.01) |
| *G01N 33/58* | (2006.01) |
| *G01N 33/92* | (2006.01) |
| *G01N 35/00* | (2006.01) |

(52) U.S. Cl.
CPC ......... *G01N 33/92* (2013.01); *G01N 35/0099* (2013.01); *G01N 2030/027* (2013.01); *G01N 2500/00* (2013.01)

(58) Field of Classification Search
CPC ......... G01N 2030/027; G01N 2500/00; G01N 33/6848; G01N 2333/665; G01N 2560/00; H01J 49/0027
See application file for complete search history.

(56) References Cited

OTHER PUBLICATIONS

Martens, Chloe, et al. "Direct protein-lipid interactions shape the conformational landscape of secondary transporters." Nature communications 9.1 (2018): 4151. (Year: 2018).*

Denisov, Ilia G., and Stephen G. Sligar. "Nanodiscs in membrane biochemistry and biophysics." Chemical reviews 117.6 (2017): 4669-4713.

Ritchie et al. "Reconstitution of membrane proteins in phospholipid bilayer nanodiscs." Methods in enzymology 464 (2009): 211-231.

Barnaba et al. "Cytochrome-P450-induced ordering of microsomal membranes modulates affinity for drugs." Angewandte Chemie International Edition 57.13 (2018): 3391-3395.

Reid et al. "Engineering nanodisc scaffold proteins for native mass spectrometry." Analytical chemistry 89.21 (2017): 11189-11192.

Keener et al. "Chemical additives enable native mass spectrometry measurement of membrane protein oligomeric state within intact nanodiscs." Journal of the American Chemical Society 141.2 (2018): 1054-1061.

Marty et al. "Probing the Lipid Annular Belt by Gas-Phase Dissociation of Membrane Proteins in Nanodiscs." Angewandte Chemie International Edition 55.2 (2016): 550-554.

Hoi, Kin Kuan, Carol V. Robinson, and Michael T. Marty. "Unraveling the composition and behavior of heterogeneous lipid nanodiscs by mass spectrometry." Analytical chemistry 88.12 (2016): 6199-6204.

Overduin, Michael, and Mansoore Esmaili. "Memtein: The fundamental unit of membrane-protein structure and function." Chemistry and physics of lipids 218 (2019): 73-84.

Brown, Michael F. "Soft matter in lipid-protein interactions." Annu. Rev. Biophys 46.1 (2017): 379-410.

Corradi et al. "Emerging diversity in lipid-protein interactions." Chemical reviews 119.9 (2019): 5775-5848.

Enkavi et al. "Multiscale simulations of biological membranes: the challenge to understand biological phenomena in a living substance." Chemical reviews 119.9 (2019): 5607-5774.

Manna, Moutusi, Tuomo Nieminen, and Ilpo Vattulainen. "Understanding the role of lipids in signaling through atomistic and multiscale simulations of cell membranes." Annual review of biophysics (2019).

Marsh, Derek. "Protein modulation of lipids, and vice-versa, in membranes." Biochimica Et Biophysica Acta (BBA)—Biomembranes 1778.7-8 (2008): 1545-1575.

Yeagle, Philip L. "Non-covalent binding of membrane lipids to membrane proteins." Biochimica et Biophysica Acta (BBA)—Biomembranes 1838.6 (2014): 1548-1559.

Bechara et al. "A subset of annular lipids is linked to the flippase activity of an ABC transporter." Nature chemistry 7.3 (2015): 255-262.

Dörr et al. "Detergent-free isolation, characterization, and functional reconstitution of a tetrameric K+ channel: the power of native nanodiscs." Proceedings of the National Academy of Sciences 111.52 (2014): 18607-18612.

Hazell et al. "Evidence of lipid exchange in styrene maleic acid lipid particle (SMALP) nanodisc systems." Langmuir 32.45 (2016): 11845-11853.

Cuevas Arenas et al. "Fast collisional lipid transfer among polymer-bounded nanodiscs." Scientific reports 7.1 (2017): 1-8.

Frick, Melissa, and Carla Schmidt. "Mass spectrometry—A versatile tool for characterising the lipid environment of membrane protein assemblies." Chemistry and physics of lipids 221 (2019): 145-157.

Robinson, Carol V. "Mass spectrometry: From plasma proteins to mitochondrial membranes." Proceedings of the National Academy of Sciences 116.8 (2019): 2814-2820.

Calabrese, Antonio N., and Sheena E. Radford. "Mass spectrometry-enabled structural biology of membrane proteins." Methods 147 (2018): 187-205.

Bayburt, Timothy H., Yelena V. Grinkova, and Stephen G. Sligar. "Self-assembly of discoidal phospholipid bilayer nanoparticles with membrane scaffold proteins." Nano letters 2.8 (2002): 853-856.

Laganowsky et al. "Membrane proteins bind lipids selectively to modulate their structure and function." Nature 510.7503 (2014): 172-175.

Mirandela et al. "The lipid environment determines the activity of the *Escherichia coli* ammonium transporter AmtB." The FASEB Journal 33.2 (2019): 1989-1999.

Nakano et al. "Static and dynamic properties of phospholipid bilayer nanodiscs." Journal of the American Chemical Society 131.23 (2009): 8308-8312.

Barnaba et al. "Lipid-exchange in nanodiscs discloses membrane boundaries of cytochrome-P450 reductase." Chemical Communications 54.49 (2018): 6336-6339.

Zhang et al. "Protein-glycosphingolipid interactions revealed using catch-and-release mass spectrometry." Analytical chemistry 84.18 (2012): 7618-7621.

Marty et al. "Bayesian deconvolution of mass and ion mobility spectra: from binary interactions to polydisperse ensembles." Analytical chemistry 87.8 (2015): 4370-4376.

Reid et al. "MetaUniDec: high-throughput deconvolution of native mass spectra." Journal of the American Society for Mass Spectrometry 30.1 (2018): 118-127.

(56)             References Cited

OTHER PUBLICATIONS

Yang, Kui, and Xianlin Han. "Accurate quantification of lipid species by electrospray ionization mass spectrometry—meets a key challenge in lipidomics." Metabolites 1.1 (2011): 21-40.

* cited by examiner

FIG. 1A

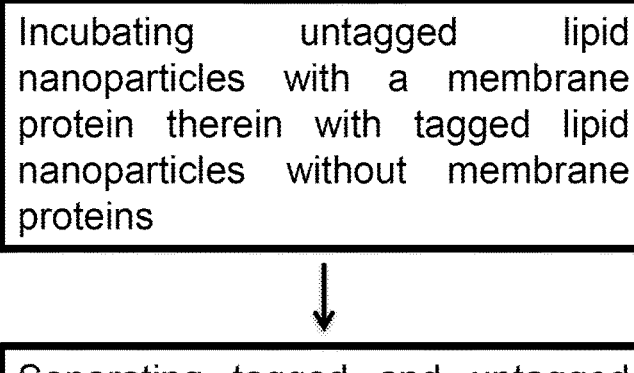

Incubating untagged lipid nanoparticles with a membrane protein therein with tagged lipid nanoparticles without membrane proteins

↓

Separating tagged and untagged lipid nanoparticles

↓

Measuring the lipid composition of the untagged lipid nanoparticles

↓

Calculating the difference between the lipid composition of both the tagged and untagged lipid nanoparticles

FIG. 1B

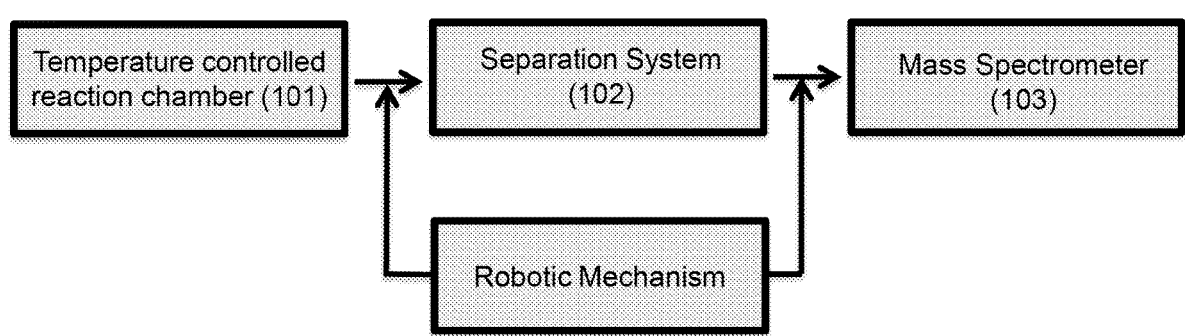

Temperature controlled reaction chamber (101)

Separation System (102)

Mass Spectrometer (103)

Robotic Mechanism

AUTOMATED LIPID EXCHANGE-MASS SPECTROMETRY SYSTEMS AND METHODS

CROSS-REFERENCES TO RELATED APPLICATIONS

This application claims benefit of U.S. Provisional Application No. 62/970,884 filed Feb. 6, 2020, the specification of which is incorporated herein in their entirety by reference.

STATEMENT REGARDING FEDERALLY SPONSORED RESEARCH OR DEVELOPMENT

This invention was made with government support under Grant No. 1845230, awarded by NSF and Grant No. R35 GM128624, awarded by National Institutes of Health. The government has certain rights in the invention.

BACKGROUND OF THE INVENTION

Field of the Invention

The present invention relates to methods and systems for measuring effects of membrane proteins on local lipid environments for various purposes, for example for determining optimal lipid environments for membrane proteins. The same methods and systems also have applications in measuring the stability of lipid nanoparticles. Lipid nanoparticles are defined broadly as any nanoscale particle with lipid components. It may include proteins, nucleic acids, and polymers as additional components.

Background Art

An important focus in membrane biology is studying how membrane proteins interact with lipids and remodel their local lipid environment. For example, lipids can play critical roles in regulating membrane protein structure and function. Further, membrane proteins are important drug targets. However, the biophysics of membrane protein-lipid interactions within lipid bilayers are often unclear because these transient, polydisperse, and competitive interactions are challenging to study.

A method to measure affinity of membrane proteins for lipids, called lipid exchange-mass spectrometry (LX-MS), utilizes mass spectrometry (MS) to monitor lipid exchange between lipoprotein nanoparticles called nanodiscs. Briefly, LX-MS uses MS to measure exchange of lipids between two populations of nanodiscs, one with embedded membrane proteins and one without embedded membrane proteins (the empty nanodiscs are tagged, the nanodiscs with the embedded protein are untagged). If a membrane protein binds a specific type of lipid, it will shift the equilibrium distribution of lipids between the nanodiscs. The equilibrium distribution can be quantitated by measuring the lipid composition in the overall population of both tagged and untagged nanodiscs combined and comparing the combined population of lipids to the population of lipids in only the untagged nanodiscs (the nanodiscs with the membrane protein embedded) after the tagged (empty) nanodiscs are removed from the total population.

BRIEF SUMMARY OF THE INVENTION

The present invention features systems, e.g., automated systems, partially automated systems, etc., for lipid exchange-mass spectrometry. The systems herein can measure the specificity of membrane protein-lipid interactions, e.g., determine the affinity of membrane proteins for binding to specific lipids, detect remodeling of the membrane environment, and determine optimal lipid composition for membrane proteins, which may be useful in structural biology and drug discovery. They can also measure the kinetics of lipid exchange between lipid nanoparticles, which may be useful in determining their stability.

The present invention features a method for measuring affinity of a membrane protein for lipids. In certain embodiments, the method comprises incubating a mixture of untagged lipid nanoparticles that may or may not contain a membrane protein, nucleic acid, or other biomolecule embedded therein with a population of tagged lipid nanoparticles without the membrane protein or other biomolecules embedded therein; separating the tagged lipid nanoparticles from the untagged lipid nanoparticles; measuring a lipid composition of the untagged lipid nanoparticles; and calculating a difference between the lipid composition of the untagged lipid nanoparticles and a lipid composition of the combination of both tagged lipid nanoparticles and untagged lipid nanoparticles. One or more of the aforementioned steps may be automated.

The present invention also features an automated system comprising one or more robotic mechanisms for performing the method described herein for measuring the affinity of a membrane protein for lipids. In some embodiments, the system may comprise a temperature controlled-reaction chamber for incubating a mixture of tagged lipid nanoparticles and untagged lipid nanoparticles at a selected temperature. In some embodiments, the system comprises a separation system for separating tagged lipid nanoparticles from untagged lipid nanoparticles. In further embodiments, the system comprises a mass spectrometer; and one or more robotic mechanisms for introducing lipid nanoparticles to or transferring lipid nanoparticles from one or a combination of the temperature controlled reaction chamber, the separation system, or the mass spectrometer.

One of the unique and inventive technical features of the present invention is the use of automated mass spectrometry to quantify lipid exchange, which enables 1) a wide range of untargeted lipids to be studied, 2) precise quantitation of individual molecular lipids, 3) simultaneous analysis of a large number of lipid species, 4) more reliable and reproducible measurements, and 5) higher throughput analysis. Without wishing to limit the invention to any theory or mechanism, it is believed that the technical feature of the present invention advantageously provides for automated analysis of the optimal lipid environment for membrane proteins and stability of lipid nanoparticles. None of the presently known prior references or work has the unique inventive technical feature of the present invention.

Furthermore, the prior references teach away from the present invention. For example, past studies of lipid exchange have required labelled lipids or only measured broad lipid classes. The present invention enables studying lipid exchange of un-labelled lipids with molecular specificity. Furthermore, the inventive technical features of the present invention contributed to a surprising result. For example, the lipid composition were titrated and an "isolipid point" where no exchange occurs, and the lipid ratio is optimal was discovered.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1A shows a flow chart diagram of the methods described herein.

FIG. 1B shows a schematic of the system for measuring the affinity of a membrane protein for lipids described herein.

DETAILED DESCRIPTION OF THE INVENTION

Figure 2A:
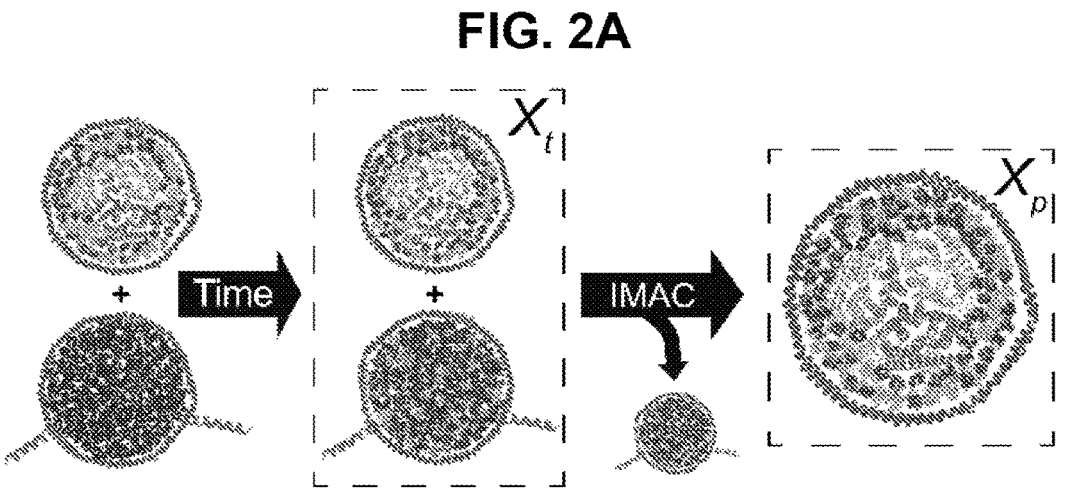
FIG. 2A shows a schematic of LX-MS between AmtB nanodiscs (AmtB is an *E. coli* ammonia channel) and empty POPC nanodiscs.

Following is a list of elements corresponding to a particular element referred to herein:

100 System for measuring membrane protein affinity for lipids

101 Temperature Controlled Reaction Center

102 Separation System

103 Mass Spectrometer

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

As used herein "lipid nanoparticles" refers broadly to any nanoscale particle with lipid components. Lipid nanoparticle may include, but are not limited to, nanodiscs as well as lipids in complex with other proteins, nucleic acids, and polymers as additional components.

As used herein, "nanodiscs" are nanoscale lipoprotein complexes comprising a lipid bilayer encircled by two membrane scaffold proteins. Examples of methods for producing nanodiscs can be found in Denisov and Sligar, 2017, Nanodiscs in Membrane Biochemistry and Biophysics. *Chem. Rev.* 117, 4669-4713; and Ritchie et al., Reconstitution of Membrane Proteins in Phospholipid Bilayer Nanodiscs, in *Methods Enzymol.*; Nejat, D., Ed.; Academic Press: San Diego, Calif., 2009; Vol. 464; pp 211-231.

As used here, "isolipid point" refers to when the lipid composition of the lipid nanoparticle comprising a membrane protein embedded therein is the same as lipid composition of the empty lipid nanoparticle.

The present invention features an automated system for lipid exchange-mass spectrometry. The system herein can measure the specificity of membrane protein-lipid interactions, e.g., determine the affinity of membrane proteins for binding to specific lipids, detect remodeling of the membrane environment, and determine optimal lipid environments or compositions for membrane proteins, which may be useful in structural biology and drug discovery. It can also measure kinetics of lipid exchange between lipid nanoparticles, which may be useful in determining their stability.

For example, the methods and systems herein may feature a membrane protein that is the subject of a drug screening or drug discovery process. The methods and systems herein may feature a membrane protein that is the subject of a structural biology study. The methods and systems herein may feature lipid nanoparticles present in a composition relating to drug or vaccine delivery for biological or synthetic drugs.

The methods herein are broadly applicable and may be appropriate for a wide range of membrane proteins and lipid nanoparticle systems.

The present invention features a method for measuring affinity of a membrane protein for lipids. In some embodiments, the method comprises incubating untagged lipid nanoparticles with a population of tagged lipid nanoparticles. In some embodiments, the untagged lipid nanoparticles comprise one or more lipids and a membrane protein. In other embodiments, the membrane protein is embedded in the untagged lipid nanoparticles. In some embodiments, the tagged lipid nanoparticles comprise one or more lipids without the membrane protein embedded therein. In other embodiments, the method comprises separating the tagged lipid nanoparticles from the untagged lipid nanoparticles. In further embodiments, the method comprises measuring the lipid composition of the untagged lipid nanoparticles. In some embodiments, the method comprises calculating a difference between the lipid composition of the untagged lipid nanoparticles and the lipid composition of the combination of both tagged lipid nanoparticles and untagged lipid nanoparticles. In some embodiments, one or more steps of the method described herein are automated.

In some embodiments, the lipid nanoparticles are nanodiscs.

The methods and systems described herein utilize two populations of lipid nanoparticles, one with (or without) embedded membrane protein and one without embedded membrane proteins. In some embodiments, the empty lipid nanoparticles are tagged and the lipid nanoparticles with the embedded protein are untagged. In other embodiments, the empty lipid nanoparticles are untagged and the lipid nanoparticles with the embedded protein are tagged. In further embodiments, both of the lipid nanoparticles are empty and can be either tagged or untagged.

In other embodiments, the lipid nanoparticles may or may not contain a biomolecule embedded therein. Non-limiting examples of biomolecules that may be embedded into a lipid nanoparticle may include but are not limited to, a membrane protein, nucleic acid, or other biomolecule.

In some embodiments, the untagged lipid nanoparticles and the tagged lipid nanoparticles have one or more types of lipids. In other embodiments, the untagged lipid nanoparticles have at least one type of lipid that is different from the one or more types of lipids of the tagged lipid nanoparticles.

In some embodiments, lipids may include but are not limited to 1-palmitoyl-2-oleoyl-sn-glycero-3-phosphocholine (POPC) or 1-palmitoyl-2-oleoyl-sn-glycero-3-phospho-(1'-racglycerol) (POPG). In other embodiments, other lipid classes may be used in the methods and systems described herein including but not limited to phosphatidylcholine, phosphatidylserine, phosphatidylglycerol, phosphatidylethanolamine, sphingomyelin, and cardiolipin lipids. The present invention is not limited to any specific type of lipid or lipid class.

In some embodiments, a mixture is prepared of untagged lipid nanoparticles comprising a membrane protein embedded therein and tagged lipid nanoparticles without the membrane protein embedded therein. In other embodiments, a mixture is prepared of tagged lipid nanoparticles comprising a membrane protein embedded therein and untagged lipid nanoparticles without a membrane protein embedded therein. In further embodiments, a mixture is prepared of tagged lipid nanoparticles without a membrane protein embedded therein and untagged lipid nanoparticles without a membrane protein embedded therein. In some embodiments, a mixture is prepared of tagged lipid nanoparticles without a membrane protein embedded therein and tagged lipid nanoparticles without a membrane protein embedded therein. In other embodiments, a mixture is prepared of untagged lipid nanoparticles without a membrane protein embedded therein and untagged lipid nanoparticles without a membrane protein embedded therein.

The methods and systems described herein utilize two populations of nanodisc, one with (or without) embedded membrane protein and one without embedded membrane proteins. In some embodiments, the empty nanodiscs are tagged and the nanodiscs with the embedded protein are untagged. In other embodiments, the empty nanodiscs are untagged and the nanodiscs with the embedded protein are tagged. In further embodiments, both of the nanodiscs are empty and can be either tagged or untagged.

In some embodiments, the lipid nanoparticles are tagged with a poly-histidine tag. In other embodiments, the lipid nanoparticles are tagged with a flag tag. In other embodiments, the lipid nanoparticles are tagged with a streptavidin tag. In some embodiments, the MSP1E3D1 scaffold protein is tagged (or untagged) in the lipid nanoparticles. In other embodiments, other scaffold proteins may be used and/or tagged in the lipid nanoparticles.

In other embodiments, a mixture is prepared of untagged nanodiscs comprising a membrane protein embedded therein and tagged nanodiscs without a membrane protein embedded therein. In some embodiments, a mixture is prepared of tagged nanodiscs comprising a membrane protein embedded therein and untagged nanodiscs without the membrane protein embedded therein. In further embodiment, a mixture is prepared of empty nanodiscs without membrane proteins embedded therein that can be either untagged, tagged, or a mixture of untagged and tagged.

In further embodiments, other lipid nanoparticles, besides nanodiscs, may also be used with various approaches to tag or distinguish the two populations. Tagging may be accomplished in different ways, for example by chemical species present on one of the two populations of lipid nanoparticles, by genetic tags added to the nanodisc MSP belt protein sequence, by size differences between the two particles, or by affixing one population to a surface.

In some embodiments, the method described herein is performed in a temperature-controlled reaction chamber. In some embodiments, untagged lipid nanoparticles and the tagged lipid nanoparticles are incubated in a temperature-controlled reaction chamber.

In other embodiments, the mixture of untagged lipid nanoparticles and tagged lipid nanoparticles is incubated for a period of time at a particular temperature, e.g., in a temperature-controlled reaction chamber. In further embodiments, a robotic mechanism mixes the untagged lipid nanoparticles with the tagged lipid nanoparticles. In other embodiments, the untagged lipid nanoparticles with the tagged lipid nanoparticles are mixed manually.

In some embodiments, the temperature of the temperature-controlled reaction chamber is between 0° C. and 50° C. In some embodiments, the temperature of the temperature-controlled reaction chamber is about 0° C. In some embodiments, the temperature of the temperature-controlled reaction chamber is about 5° C. In some embodiments, the temperature of the temperature-controlled reaction chamber is about 10° C. In some embodiments, the temperature of the temperature-controlled reaction chamber is about 15° C. In some embodiments, the temperature of the temperature-controlled reaction chamber is about 20° C. In some embodiments, the temperature of the temperature-controlled reaction chamber is about 25° C. In some embodiments, the temperature of the temperature-controlled reaction chamber is about 30° C. In some embodiments, the temperature of the temperature-controlled reaction chamber is about 35° C. In some embodiments, the temperature of the temperature-controlled reaction chamber is about 40° C. In some embodiments, the temperature of the temperature-controlled reaction chamber is about 45° C. In some embodiments, the temperature of the temperature-controlled reaction chamber is about 50° C. In some embodiments, the temperature of the temperature-controlled reaction chamber is greater than 50° C.

In some embodiments, the lipid nanoparticle mixture is incubated for a period of time ranging from a few seconds to a few days. In some embodiments, the lipid nanoparticle mixture is incubated for about 10 seconds. In some embodiments, the lipid nanoparticle mixture is incubated for about 1 minute. In some embodiments, the lipid nanoparticle mixture is incubated for about 10 minutes. In some embodiments, the lipid nanoparticle mixture is incubated for about 30 minutes. In some embodiments, the lipid nanoparticle mixture is incubated for about 1 hour. In some embodiments, the lipid nanoparticle mixture is incubated for about 12 hours. In some embodiments, the lipid nanoparticle mixture is incubated for about 1 day. In some embodiments, the lipid nanoparticle mixture is incubated for about 2 days. In some embodiments, the lipid nanoparticle mixture is incubated for about 5 days. In some embodiments, the lipid nanoparticle mixture is incubated for longer than 5 days.

In some embodiments, the lipid nanoparticle mixture is mixed by the robotic mechanism through pipetting the lipid nanoparticle mixture once. In some embodiments, method further comprises a robotic mechanism mixing the untagged lipid nanoparticles with the tagged lipid nanoparticles before incubating the untagged lipid nanoparticles and the tagged lipid nanoparticles.

In some embodiments, separating the tagged lipid nanoparticles from the untagged lipid nanoparticles comprises introducing the mixture of untagged lipid nanoparticles and tagged lipid nanoparticles to a separation system. In some embodiments, a robotic mechanism introduces the mixture of untagged lipid nanoparticles and tagged lipid nanoparticles to the separation system.

In some embodiments, the tagged lipid nanoparticles are separated from the untagged nanodiscs via a separation system. In other embodiments, the separating the tagged lipid nanoparticles from the untagged lipid nanoparticles comprises introducing the mixture of untagged lipid nanoparticles and tagged lipid nanoparticles to a separation system. In certain embodiments, a robotic mechanism introduces the mixture of untagged lipid nanoparticles and tagged lipid nanoparticles to the separation system. In some embodiments, a separation system may include but is not limited to a chromatography system such as an affinity chromatography system or a size-exclusion chromatography system. A non-limiting example of affinity chromatography is immobilized metal affinity chromatography (IMAC).

In certain embodiments, the untagged lipid nanoparticles are collected or concentrated via a collection system, such as a chromatography system. In some embodiments, the untagged lipid nanoparticles are introduced to a collection system for capturing the untagged lipid nanoparticles. A non-limiting example of a chromatography system for collecting or concentrating the untagged lipid nanoparticles includes liquid chromatography (LC). In further embodiments, the separation system removes the tagged lipid nanoparticles from the untagged lipid nanoparticles. The present invention is not limited to the aforementioned collection systems or chromatography systems.

In some embodiments, the lipid composition of the untagged lipid nanoparticles is measured. In other embodiments, the difference between the lipid composition of the untagged lipid nanoparticles is compared to the lipid composition of the combined lipid nanoparticles (untagged and tagged). In some embodiments, measuring the lipid composition of the untagged lipid nanoparticles comprises subjecting the untagged lipid nanoparticles to mass spectrometry. In other embodiments, measuring the lipid composition of the tagged lipid nanoparticles comprises subjecting the tagged lipid nanoparticles to mass spectrometry. In further embodiments, measurements of lipid composition may be made via mass spectrometry (MS). Mass spectrometry methods may include but are not limited to electrospray ionization mass spectrometry (ESI-MS) and liquid chromatography mass spectrometry (LC/MS).

In some embodiments, the untagged lipid nanoparticles captured by the collection system are subsequently subjected to mass spectrometry for measuring the lipid composition of the untagged lipid nanoparticles.

In certain embodiments, one or more of the aforementioned steps in the methods described herein are automated. For example, a robotic mechanism may mix the untagged lipid nanoparticles with the tagged lipid nanoparticles. In certain embodiments, a robotic mechanism introduces the mixture of untagged lipid nanoparticles and tagged lipid nanoparticles to the separation system. In certain embodiments, a robotic mechanism introduces the untagged lipid nanoparticles to the collection system. In certain embodiments, a robotic mechanism introduces the untagged lipid nanoparticles to mass spectrometry.

In certain embodiments, one or more of the aforementioned steps in the methods described herein are automated and carried out by a robotic mechanism. In some embodiments, the mixture of lipid nanoparticles is mixed by a robotic mechanism. In other embodiments, the mixture of lipid nanoparticles is mixed once by pipetting the mixture up and down several times by a robotic mechanism. In some embodiments, the robotic mechanism injects the lipid nanoparticle mixture into a separation system. In other embodiments, the robotic mechanism injects the lipid nanoparticle mixture onto a liquid chromatography separation system. In further embodiments, a series of pumps and valves allow the lipid nanoparticle mixture to be separated and then injected into the mass spectrometer.

As used herein, a "robotic mechanism" refers to a mechanized liquid handling system, including a syringe and needle or pipette capable of aspirating or dispensing liquids in specified containers and locations via a robotic arm. It may also include a system of computer-controlled pumps and valves, such as a chromatography system, that enables liquids to be moved and injected for separations or mass spectrometry analysis.

As a non-limiting example, in certain embodiments, the two populations of lipid nanoparticles would be mixed by the robotic mechanism (or by hand) and allowed to incubate at a set temperature for a specific time. Then, the robotic mechanism would inject the sample onto an immobilized metal affinity chromatography (IMAC) column to remove the tagged lipid nanoparticles. The flow-through would be captured on a liquid chromatography (LC) column. Lipids would then be eluted off the LC column for quantitation by mass spectrometry.

In some embodiments, the method described herein is for determining an optimal lipid environment for a membrane protein.

As used herein, "an optimal lipid environment" refers to a state where the relative ratios of lipid components directly bound to a membrane protein is equal to the relative ratios of lipid components in the bulk lipid membrane.

As used herein, "a membrane protein" refers to a protein that interacts with or can be embedded within a lipid bilayer membrane. In some embodiments, the membrane protein is a protein that is the subject of a structural biology study. In other embodiments, the membrane protein is a protein that is a subject of a drug screening or drug discovery process.

The present invention may further feature a system (100) for measuring affinity of a membrane protein for lipids. In some embodiments, the system (100) comprises a temperature controlled-reaction chamber (101) for incubating a mixture of tagged lipid nanoparticles and untagged lipid nanoparticles at a selected temperature. In other embodiments, the system (100) comprises a separation system (102) for separating tagged lipid nanoparticles from untagged lipid nanoparticles. In some embodiments, the system (100) comprises a mass spectrometer (103). In further embodiments, the system comprises one or more robotic mechanisms for introducing lipid nanoparticles to or transferring lipid nanoparticles from one or a combination of any of the aforementioned parts of the system.

In some embodiments, the one or more robotic mechanisms are capable of performing one or a combination of actions: introducing a mixture to the temperature controlled-reaction chamber; mixing the mixture in the temperature controlled-reaction chamber; transferring the mixture in the temperature controlled-reaction chamber to the separation system; or transferring untagged lipid nanoparticles to the mass spectrometer.

In some embodiments, one or more robotic mechanisms are capable of performing one or a combination of the following actions: incubating a mixture of untagged lipid nanoparticles comprising a membrane protein embedded therein with a population of tagged lipid nanoparticles without the membrane protein embedded therein; separating the tagged lipid nanoparticles from the untagged lipid nanoparticles; or measuring a lipid composition of the untagged lipid nanoparticles.

In some embodiments, the system comprises separate physical devices (i.e. a temperature controlled-reaction chamber, a separation system and a mass spectrometer as individual devices). In other embodiments, the system comprises devices that are connected together as a workflow of connected devices rather than a single device. In some embodiments, the devices are connected together through robotic mechanisms.

In some embodiments, the system further comprising a memory having computer executable instructions for calculating a difference between the lipid composition of the untagged lipid nanoparticles and a lipid composition of the combination of both tagged lipid nanoparticles and untagged lipid nanoparticles.

In some embodiments, the system described herein can perform any of the methods described herein.

EXAMPLE

The following is a non-limiting example of the present invention. It is to be understood that said example is not intended to limit the present invention in any way. Equivalents or substitutes are within the scope of the present invention.

Lipids slowly exchange between nanodiscs, ultimately leading two distinct populations of empty nanodiscs with different lipids to equilibrate to the same lipid composition. Without wishing to limit the present invention to any theory or mechanism it is believed that the exchange between nanodiscs likely follows a monomer diffusion model, where the rate limiting step is diffusion of a monomeric lipid out of the nanodisc into free solution rather than a collision between two nanodiscs.

It was hypothesized that embedding an integral membrane protein in one population of nanodiscs would shift the equilibrium distribution of lipids between the two populations, e.g., binding of one lipid type to the membrane protein would enrich the membrane protein nanodiscs in the bound lipid type according to Le Chatelier's principle. The two populations of nanodiscs are mixed for exchange and then separated prior to analysis using a tag on the empty nanodisc population.

AmtB, an *E. coli* ammonia channel, was incorporated into untagged nanodiscs with 50/50 1-palmitoyl-2-oleoyl-sn-glycero-3-phosphocholine (POPC)/1-palmitoyl-2-oleoyl-sn-glycero-3-phospho-(1'-racglycerol) (POPG). Polyhistidine-tagged empty nanodiscs without AmtB were also prepared at various POPC/POPG ratios ranging from 0 to 100% POPC. In one embodiment, the ratios were 0%, 20%, 40%, 50%, 60%, 80%, and 100% POPC Tagged empty nanodiscs were mixed with untagged AmtB nanodiscs, and the mixture was allowed to exchange at room temperature (21-23° C.) over 2.8 days. After exchange, internal standards containing PC and PG lipids with different tail lengths were added, and the total lipid mole fraction of POPC, $X_t$, was measured (tagged and untagged) by direct infusion MS. Then, the tagged empty nanodiscs were removed by passing the mixture over immobilized metal affinity chromatography (IMAC) beads, and the untagged AmtB nanodiscs were measured alone to determine the lipid mole fraction in the membrane protein nanodiscs, $X_p$. Preliminary experiments confirmed that the exchange was within experimental error (typically 2-4% absolute mole fraction) by 2.8 days, but a full examination of kinetics was not performed due to limited amounts of sample. Control experiments without AmtB showed that empty nanodiscs equilibrated to a nearly uniform lipid composition between tagged and untagged nanodiscs.

Figure 2B:
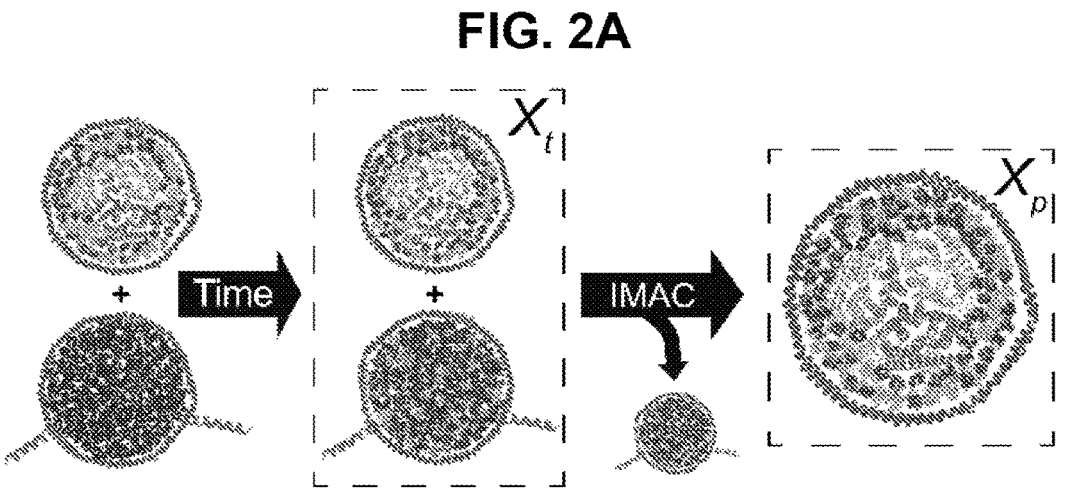
FIG. 2B shows a fit (solid line) of the percentage mole fraction of POPC difference between AmtB nanodiscs and total lipids ($X_p$–$X_t$) vs. the total percentage mole fraction ($X_e$) shows the isolipid point at 24±2% POPC. Preference of AmtB for POPC or POPG is shaded above and below respectively.

Comparing the total lipid composition (tagged and untagged) with the AmtB nanodiscs (untagged) revealed clear inhomogeneities in lipid distributions. FIGS. 2A and 2B shows the difference in POPC mole fraction between the AmtB nanodiscs and the total $(X_p-X_t)$ as a function of $X_t$. At high total POPC, AmtB shifted the equilibrium to acquire more POPG in the AmtB nanodiscs. Conversely, at low POPC levels, AmtB shifted the equilibrium to enrich the AmtB nanodiscs in POPC. In other words, AmtB remodeled the local lipid environment towards a more optimal lipid distribution, which resulted in an unequal partitioning of lipids between empty nanodiscs and AmtB nanodiscs.

After establishing that AmtB remodels the local membrane environment, $X_t$ versus $X_p-X_t$ was fit to a sigmoidal curve and the x-intercept where $X_p-X_t=0$ was determined. At this mole fraction, which is termed the isolipid point, the lipid composition of the membrane protein nanodiscs is the same as the empty nanodiscs. The composition of the annular lipids matches the bulk lipid bilayer at the isolipid point. For AmtB, the isolipid point was found to be 24±2% POPC or 76±2% POPG.

Thus, the methods of the present invention demonstrate that AmtB has a clear preference for POPG and will remodel its surrounding lipid membrane to enrich in POPG.

However, it does have some affinity for POPC and will enrich the surrounding membrane in POPC if not enough is present. Overall, the optimal ratio for AmtB is 24/76 POPC/POPG, which is the isolipid point for this system.

Methods

Protein Expression and Purification

HIS-MBP-TEV-AmtB and membrane scaffold protein MSP1E3D1 were expressed in *E. coli* and purified as previously described. Briefly, AmtB was purified by immobilized metal affinity chromatography (IMAC) followed by size exclusion chromatography (SEC) with a Superdex 200 16/600 (GE Healthcare) in 0.025% dodecylmaltoside (DDM, Anatrace) buffer. MSP1E3D1 was purified by IMAC using established protocols.

Nanodisc Assembly and Purification

AmtB nanodiscs were assembled using MSP1E3D1(−) or added threonine variants to accommodate the large AmtB trimer and prepared similar to as previously described. MSP1E3D1(−) is the cleaved version of MSP1E3D1 where the polyhistidine tag has been removed. 1-Palmitoyl-2-oleoyl-sn-glycero-3-phosphocholine (POPC) and 1-palmitoyl-2-oleoyl-sn-glycero-3-phospho-(1'-racglycerol) (POPG) lipids from Avanti Polar Lipids were dissolved in chloroform and quantified by phosphate analysis. Lipid were dried and resuspended in 100 mM sodium cholate (Sigma Aldrich) prior to being mixed to the desired POPC/POPG ratio. The reconstitution mixture of purified AmtB in DDM, mixed lipids in cholate, and MSP were incubated on ice for approximately 1 hour before adding Amberlite XAD-2 beads (Sigma Aldrich) for overnight detergent removal and nanodisc self-assembly at 4° C. Empty nanodiscs were removed by IMAC, and membrane protein nanodiscs were further purified by SEC. Following overnight cleavage of the HIS-MBP tag with TEV protease, AmtB nanodiscs were then purified through another round of IMAC and SEC to isolate monodisperse nanodiscs with cleaved AmtB. Here, 0.2 M ammonium acetate at pH 6.8 (Sigma Aldrich) was used as the mobile phase for SEC to exchange the AmtB nanodiscs into an MS-compatible buffer. Samples were concentrated to 1-5 μM and flash frozen at −80° C. for storage. Because the polyhistidine tag was removed from both AmtB and MSP1E3D1(−), there was no polyhistidine tag on the AmtB nanodiscs.

Empty nanodiscs without membrane proteins were assembled and purified in a similar manner, as previously described. Here, either the polyhistidine tagged MSP1E3D1 or the untagged MSP1E3D1(−) was used. Lipid stocks of POPC and POPG were prepared in cholate and mixed to the desired ratio prior to assembly.

For both lipid exchange and native MS, error bars are shown as the standard deviation of single measurements on three replicate nanodisc assemblies that were prepared separately.

Lipid Exchange

The 50% POPC AmtB nanodiscs were mixed with empty nanodiscs assembled with the polyhistidine tagged MSP1E3D1 in POPC/(POPC+POPG) mole fractions of 0, 20, 40, 60, 80, or 100% at a 1:1 molar ratio and a final concentration of 2.3 μM AmtB nanodiscs. To extend the titration to a lower total POPC mole fraction ($X_t$), the AmtB nanodiscs were mixed with 0% POPC empty nanodiscs at a 1:2.6 molar ratio while keeping the AmtB nanodiscs at 2.3 μM. The mixtures were incubated at room temperature (21-23° C.) for 2.8 days to allow the lipid exchange to reach equilibrium. Preliminary experiments showed that exchanges at longer time points were within experimental error of exchanges at 2.8 days, demonstrating that the solution was approached equilibrium by 2.8 days. Control experiments were also performed using 50% POPC untagged empty nanodiscs mixed with empty nanodiscs assembled with the polyhistidine-tagged MSP1E3D1 in POPC/(POPC+POPG) mole fractions of 0, 20, 40, 60, 80, or 100% at a 1:1 molar ratio and a final concentration of 2.3 μM MSP as well as at a 1:2.6 molar ratio with 0% nanodiscs.

Separation of Exchanged Nanodiscs

After exchanging, tagged empty nanodiscs and untagged (either empty or AmtB) nanodiscs were separated by IMAC using a Ni-NTA His SpinTrap (GE Healthcare). Because small exchange volumes of roughly 16 μL were used, around ⅓ of the 100 μL column volume was removed for a final column volume around 66 μL. The SpinTrap was prepared by three washes of 450 μL loading buffer (20 mM imidazole, 0.2 M ammonium acetate, pH 7.6) to equilibrate the column. Prior to addition to the beads, the imidazole concentration of the exchange mixture was adjusted to 20 mM by adding a 1 M imidazole solution (pH 7.6 adjusted with acetic acid) to limit the non-specific binding of the untagged nanodiscs. Then, the exchange reaction mixture was added to the IMAC beads and allowed to incubate for 1-2 minutes at 4° C. The flow-through was removed by centrifugation at 100 g for 45 seconds, and extra loading buffer of 20 μL was added to the column and washed under the same centrifugation procedures. Preliminary tests with only untagged nanodiscs showed that the concentration of nanodiscs was highest in the first wash due to the small volumes of sample used. Thus, the first wash was collected for MS analysis to maximize the lipid concentration. Around 20 μL was typically recovered. After separation, the His SpinTrap was cleaned with three washes of 450 μL elution buffer (400 mM imidazole, 0.2 M ammonium acetate, pH 7.8). The tagged empty nanodiscs were not recovered nor analyzed. Collection of the eluted tagged nanodiscs was not attempted to simplify the experiment, avoid sample cleanup to remove the 0.4 M imidazole, and so that nonspecific binding of untagged nanodiscs was not a concern.

Mass Spectrometry Analysis of Lipid Exchange

Because PC and PG lipids ionize best in positive and negative mode respectively, measurements were made in both ionization modes through separate injections. Lipid ionization efficiency is dominated by the head groups, so lipids with the same head groups but different tail lengths as internal standards were used: 1,2-dimyristoyl-sn-glycero-3-phosphocholine (DMPC) and 1,2-dimyristoyl-sn-glycero-3-phospho-(1'-rac-glycerol) (DMPG). Internal standards were dissolved separately in chloroform, and their concentrations were measured by phosphate analysis. Immediately after quantification, both standards were mixed to a 1:1 molar ratio in a glass tube, dried together, and resuspend in methanol to a final concentration around 3 mM. This stock solution of internal standards was then diluted 30-50 fold before addition to nanodisc samples.

Prior to analysis, nanodisc samples—either before (tagged and untagged) or after (untagged only) IMAC separation—were mixed with 10 μL of diluted internal standard to a final methanol concentration of 30-40% and a final volume around 30 μL. The sample was vortexed to ensure complete mixing of the internal standard. An Agilent 1260 Infinity II HPLC system was used to perform the direct flow injection of 5 μL of samples to the MS. Each flow injection was 3 minutes at a flow rate of 80 μL/min. No LC was required because the lipid mixtures were very simple, and the exchange was performed in MS-compatible ammonium acetate buffers. Positive ionization mode was used to analyze PC lipids using a 90% methanol with 0.1% formic acid solvent. Negative ionization mode was used to analyze PG lipids using 90% methanol with 0.1% ammonium hydroxide. The injection needle was washed with 5% acetonitrile after each injection, and two blanks of methanol were injected between each sample injection to ensure no carryover of the previous sample.

Mass spectrometry was performed using a Waters Micromass Quattro Micro triple quadrupole mass spectrometer with ESI source. Key tune parameters were:

Positive Mode: 3.3 kV capillary voltage, 35 V cone voltage, 4 V extractor voltage, 100° C. source temperature, 150° C. desolvation temperature, and the desolvation gas flow at 105.8 L/hr.

Negative Mode: −3.3 kV capillary voltage, −30 V cone voltage, −3 V extractor voltage, 100° C. source temperature, 150° C. desolvation temperature, and the desolvation gas flow at 250 L/hr.

1For positive mode, full scans were collected over a mass range of 100-1000 m/z using a 1 second scan time and 0.1 second inter-scan delay. The monoisotopic peak of both the POPC and DMPC were integrated to get the signal intensity from each.

For negative mode, selected ion monitoring was used because the negative mode signal was generally lower. Here, a 0.25 second dwell time was used at the monoisotopic m/z of POPG and DMPG with a 0 span, 0.02 s inter-channel delay, and 0.02 second inter-scan delay.

Lipid Exchange Data Analysis

To quantify the relative mole fractions of POPC and POPG, the intensities measured by MS ($I_{POPC}$ and $I_{POPG}$) were normalized by dividing by the intensities of the internal standards, DMPC and DMPG respectively ($I_{DMPC}$ and $I_{DMPG}$). Because internal standards were prepared in a 1:1 molar ratio of DMPC:DMPG, the normalized signals could then be compared directly.

Thus, the relative mole fraction, X, of POPC was calculated as:

$$\frac{\dfrac{I_{POPC}}{I_{DMPC}}}{\dfrac{I_{POPC}}{I_{DMPC}} + \dfrac{I_{POPG}}{I_{DMPG}}}$$

Mole fractions are shown as percentages rather than ratios for simplicity.

To determine the isolipid point, the plot of $X_t$ versus $X_p-X_t$ was fit to a sigmoidal curve of the following form $$y = a + \frac{b}{1 + e^{-c(x-d)}}$$

in Python using the SciPy library. The fit was global across all three replicates. The equation with fit parameters was then solved to determine the $X_t$ value (x) where $y=X_p-X_t=0$, the isolipid point. The uncertainty of the isolipid point was determined with bootstrapping using random sampling with replacement.

LX-MS Method Validation

To validate that the internal standards had similar ionization efficiencies to the analyte lipids, known mixtures of DMPC/POPC or DMPG/POPG in methanol were created with a board range of ratios from 0.2:1 to 20:1. The measured ratios of $$\frac{I_{POPC}}{I_{DMPC}} \text{ or } \frac{I_{POPG}}{I_{DMPG}}$$

versus their expected values both showed linear responses with slopes close to 1.

To validate that the mole fraction of POPC was accurate, three known mixtures of POPC and POPG in methanol were prepared with different POPC mole fractions (25, 50, and 75% POPC). These three known mixtures were analyzed daily as described above to confirm the measurement accuracy. The absolute standard deviations of the measurements were all around 2-4% POPC and were less than one standard deviation from the known mole fraction.

The method was also validated with nanodiscs prepared at known lipid compositions. Untagged empty nanodiscs prepared with 0, 25, 50, 75, and 100% POPC and AmtB nanodiscs with 50% POPC were measured as described herein. Similar to known lipid mixtures in methanol, nanodiscs showed an absolute measurement standard deviation around 2-4% POPC and were generally within one standard deviation of the known mixture.

To validate the IMAC separation, the untagged nanodiscs with known ratios (0, 25, 50, 75, and 100%) were added to the IMAC beads and then collected as described. The same analysis was also performed for the 50% POPC AmtB nanodiscs to verify that there was no significant change in lipid mole fraction due to the separation. The capture of tagged empty nanodiscs was validated by performing the same separation and analysis procedure on tagged nanodiscs alone. Here, no measurable amount of POPC or POPG was detected, confirming that the contribution of uncaptured tagged nanodiscs is negligible.

Finally, whether flipping the starting lipid composition would influence the final distribution was also tested. Here, duplicate assemblies of AmtB nanodiscs were prepared with 0% POPC (100% POPG) and were exchanged with 50% tagged empty nanodiscs. The $X_t$ values were higher than the mixture of 50% AmtB nanodiscs with 0% empty nanodiscs because AmtB displaces lipids from the nanodisc, leading to more POPC in the total lipid pool for the flipped experiment. Nevertheless, the results were consistent with the curve in FIG. 2B, demonstrating that the equilibrium $X_p-X_t$ differences were independent of the starting lipid composition.

Embodiments of the present invention can be freely combined with each other if they are not mutually exclusive.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method for measuring affinity of a membrane protein for lipids, said method comprising:
    a) incubating untagged lipid nanoparticles with a population of tagged lipid nanoparticles, wherein the untagged lipid nanoparticles comprise one or more lipids and a membrane protein, wherein the membrane protein is embedded in the untagged lipid nanoparticles, wherein the tagged lipid nanoparticles comprise one or more lipids without the membrane protein embedded therein;
    b) separating the tagged lipid nanoparticles from the untagged lipid nanoparticles;
    c) measuring a lipid composition of the untagged lipid nanoparticles; and
    d) calculating a difference between the lipid composition of the untagged lipid nanoparticles and a lipid composition of the combination of both tagged lipid nanoparticles and untagged lipid nanoparticles;
    wherein one or more of steps (a)-(d) are automated.

2. The method of claim 1, wherein the lipid nanoparticle is a nanodisc.

3. The method of claim 1, wherein the untagged lipid nanoparticles and the tagged lipid nanoparticles have one or more types of lipids, and wherein the untagged lipid nanoparticles have at least one type of lipid that is different from the one or more types of lipids of the tagged lipid nanoparticles.

4. The method of claim 1, wherein step (a) is performed in a temperature-controlled reaction chamber.

5. The method of claim 1, wherein the method further comprises a robotic mechanism for mixing the untagged lipid nanoparticles with the tagged lipid nanoparticles before incubating the untagged lipid nanoparticles and the tagged lipid nanoparticles.

6. The method of claim 1, wherein separating the tagged lipid nanoparticles from the untagged lipid nanoparticles comprises a robotic mechanism introducing the mixture of untagged lipid nanoparticles and tagged lipid nanoparticles to a separation system.

7. The method of claim 6, wherein the separation system is a chromatography system, wherein the chromatography system is affinity chromatography.

8. The method of claim 6, wherein the separation system removes the tagged lipid nanoparticles and captures the untagged lipid nanoparticles.

9. The method of claim 8, wherein capturing the untagged lipid nanoparticles comprises a robotic mechanism introducing the untagged lipid nanoparticles to a collection system.

10. The method of claim 9, wherein the collection system is a chromatography system, wherein the chromatography system is liquid chromatography (LC).

11. The method of claim 9, wherein the untagged lipid nanoparticles captured by the collection system are subsequently subjected to mass spectrometry for measuring the lipid composition of the untagged lipid nanoparticles.

12. The method of claim 1, wherein the method is for determining an optimal lipid environment for a membrane protein.

13. The method of claim 12, wherein the membrane protein is a protein that is the subject of a drug screening or drug discovery process.

14. A system (100) for measuring affinity of a membrane protein for lipids using the method of claim 1, said system comprising:
   a) a temperature controlled-reaction chamber (101) for incubating a mixture of tagged lipid nanoparticles and untagged lipid nanoparticles at a selected temperature;
   b) a separation system (102) for separating tagged lipid nanoparticles from untagged lipid nanoparticles;
   c) a mass spectrometer (103); and
   d) one or more robotic mechanisms for introducing lipid nanoparticles to or transferring lipid nanoparticles from one or a combination of (a)-(c).

15. The system of claim 14, wherein the lipid nanoparticles are nanodiscs.

16. The system of claim 14, wherein the separation system is a chromatography system, wherein the chromatography system is affinity chromatography.

17. The system of claim 14, wherein the one or more robotic mechanisms are capable of performing one or a combination of the following actions:
   a) mixing the mixture in the temperature controlled-reaction chamber;
   b) introducing a mixture to the temperature controlled-reaction chamber;
   c) transferring the mixture in the temperature controlled-reaction chamber to the separation system; or
   d) transferring untagged lipid nanoparticles to the mass spectrometer.

18. The system of claim 14, wherein the one or more robotic mechanisms are capable of performing one or a combination of the following actions:
   a) incubating the untagged lipid nanoparticles having the membrane protein embedded therein with the tagged lipid nanoparticles without the membrane protein embedded therein;
   b) separating the tagged lipid nanoparticles from the untagged lipid nanoparticles; and
   c) measuring a lipid composition of the untagged lipid nanoparticles.

19. The system of claim 18, wherein the system further comprising a memory having computer executable instructions for calculating a difference between the lipid composition of the untagged lipid nanoparticles and a lipid composition of the combination of both tagged lipid nanoparticles and untagged lipid nanoparticles.

20. The system of claim 18, wherein the untagged lipid nanoparticles and the tagged lipid nanoparticles have one or more types of lipids, and wherein the untagged lipid nanoparticles have at least one type of lipid that is different from the one or more types of lipids of the tagged lipid nanoparticles.

\* \* \* \* \*